(12) United States Patent
Sharkey et al.

(10) Patent No.: US 6,645,203 B2
(45) Date of Patent: Nov. 11, 2003

(54) SURGICAL INSTRUMENT WITH OFF-AXIS ELECTRODE

(75) Inventors: Hugh R. Sharkey, Menlo Park, CA (US); Gary S. Fanton, Portola Valley, CA (US); Remberto J. Carranza, So. San Francisco, CA (US); Douglas M. Lorang, Santa Clara, CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 09/753,786

(22) Filed: Jan. 2, 2001

(65) Prior Publication Data

US 2001/0023347 A1 Sep. 20, 2001

Related U.S. Application Data

(63) Continuation-in-part of application No. 09/022,688, filed on Feb. 12, 1998, now Pat. No. 6,168,593.
(60) Provisional application No. 60/037,620, filed on Feb. 12, 1997.

(51) Int. Cl.[7] .............................................. A61B 18/18
(52) U.S. Cl. ............................. 606/41; 606/48; 606/49; 606/50
(58) Field of Search ................................ 607/101–102; 606/34, 32, 41–51

(56) References Cited

U.S. PATENT DOCUMENTS

| 164,184 A | 8/1875 | Kidder |
| 300,155 A | 6/1884 | Starr |
| 371,664 A | 10/1887 | Brannan et al. |
| 452,220 A | 5/1891 | Gunning |
| 1,314,855 A | 9/1919 | Carpenter |

(List continued on next page.)

FOREIGN PATENT DOCUMENTS

| DE | 3511107 A1 | 10/1986 | ............ A61B/17/39 |
| DE | 3632197 A1 | 3/1988 | ............ A61B/10/00 |
| DE | 39 18316 | 3/1990 | ............ A61B/17/39 |
| EP | 0 257 116 A1 | 3/1988 | ............ A61N/1/36 |
| EP | 0 274 705 A1 | 7/1988 | ........... A61M/23/00 |

(List continued on next page.)

OTHER PUBLICATIONS

Lee Beadling, *Bi–Polar electrosurgical devices: Sculpting the future of arthroscopy*, Orthopedics Today, Jan. 1997, vol. 17, No. 1, Slack, Inc., Medical Publisher.
Cosset, J.M., Resistive Radiofrequency (Low Frequency) Interstitial Heating (RF Technique), Interstitial Hyperthermia, Dec. 6, 1993, pp. 3–5, 37.
Ellman International Mfg., Inc., 1989, Catalog, pp. 1–5, 20.
Attachment I: Competetive Literature on Generators with Bipolar Capabilities, IME Co., Ltd. pp. 60–86.
Attachment II: Competetive Literature on Bipolar Forceps and Footswitch Controls, IME Co., Ltd. pp. 87–104.
Christian, C. et al., "Allograft Anterior Cruciate Ligament Reconstruction with Patellar Tendon: An Endoscopic Technique", *Operative Techniques in Sports Medicine*, vol. 1, No. 1, Jan. 1993, pp. 50–57.

(List continued on next page.)

*Primary Examiner*—Linda C. M. Dvorak
*Assistant Examiner*—D. Ruddy
(74) *Attorney, Agent, or Firm*—Fish & Richardson P.C.

(57) ABSTRACT

A surgical instrument comprising a handle and an elongated probe connected to the handle. The elongated probe has a terminus distal to the handle. At least one electrode that includes an electrode surface is positioned on the terminus so that a line from a geometric center of the electrode surface and substantially perpendicular to the electrode surface intersects at an angle a longitudinal axis formed by the elongated probe. A conductor is provided for attaching the at least one electrode to the handle.

15 Claims, 8 Drawing Sheets

U.S. PATENT DOCUMENTS

| | | |
|---|---|---|
| 1,366,756 A | 1/1921 | Wappler |
| 1,731,627 A | 10/1929 | Johnson et al. |
| 1,735,271 A | 12/1929 | Groff |
| 1,814,791 A | 7/1931 | Ende |
| 1,908,583 A | 5/1933 | Wappler |
| 1,916,722 A | 7/1933 | Ende |
| 1,932,258 A | 10/1933 | Wappler |
| 1,943,543 A | 1/1934 | McFadden |
| 1,983,669 A | 11/1934 | Kimble |
| 2,002,594 A | 5/1935 | Wappler et al. |
| 2,004,559 A | 6/1935 | Wappler et al. |
| 2,050,904 A | 8/1936 | Trice |
| 2,056,377 A | 10/1936 | Wappler |
| 2,090,923 A | 8/1937 | Wappler ................. 128/303.15 |
| 2,224,464 A | 12/1940 | Wolf |
| 2,275,167 A | 3/1942 | Bierman |
| 2,888,928 A | 6/1959 | Seiger |
| 3,152,590 A | 10/1964 | Zurdo et al. |
| 3,163,165 A | 12/1964 | Isakawa |
| 3,178,728 A | 4/1965 | Christensen ....................... 3/1 |
| 3,460,539 A | 8/1969 | Anhalt, Sr. |
| 3,579,643 A | 5/1971 | Morgan ............................. 3/1 |
| 3,595,239 A | 7/1971 | Petersen |
| 3,768,482 A | 10/1973 | Shaw |
| 3,776,230 A | 12/1973 | Neefe ......................... 128/260 |
| 3,828,780 A | 8/1974 | Morrison, Jr. |
| 3,856,015 A | 12/1974 | Iglesias ................. 128/303.15 |
| 3,867,728 A | 2/1975 | Substad et al. ..................... 3/1 |
| 3,870,047 A | 3/1975 | Gonser |
| 3,879,767 A | 4/1975 | Substad ............................. 3/1 |
| 3,886,600 A | 6/1975 | Kahn et al. ......................... 3/1 |
| 3,901,242 A | 8/1975 | Storz |
| 3,902,494 A | 9/1975 | Haberlin |
| 3,920,021 A | 11/1975 | Hilterbrandt |
| 3,920,022 A | 11/1975 | Pastor |
| 3,938,198 A | 2/1976 | Kahn et al. ................... 3/1.912 |
| 3,938,527 A | 2/1976 | Rioux et al. |
| 3,945,375 A | 3/1976 | Banko ........................... 128/6 |
| 3,987,499 A | 10/1976 | Scharbach et al. ............ 3/1.91 |
| 3,987,795 A | 10/1976 | Morrison |
| 3,992,725 A | 11/1976 | Homsy ............................. 3/1 |
| 4,043,342 A | 8/1977 | Morrison, Jr. ......... 128/303.15 |
| 4,074,718 A * | 2/1978 | Morrison, Jr. .......... 606/115 |
| 4,085,466 A | 4/1978 | Goodfellow et al. .......... 3/1.91 |
| 4,129,470 A | 12/1978 | Homsy ....................... 156/155 |
| 4,134,406 A | 1/1979 | Iglesias ................. 128/303.15 |
| 4,224,696 A | 9/1980 | Murray et al. ................ 3/1.911 |
| 4,224,697 A | 9/1980 | Murray et al. ................ 3/1.911 |
| 4,326,529 A | 4/1982 | Doss et al. ............... 128/303.1 |
| 4,344,193 A | 8/1982 | Kenny ........................ 3/1.911 |
| 4,362,160 A | 12/1982 | Hiltebrandt ............ 128/303.15 |
| 4,375,220 A | 3/1983 | Matvias ...................... 128/804 |
| 4,381,007 A | 4/1983 | Doss ........................ 128/303.1 |
| 4,397,314 A | 8/1983 | Vaguine ...................... 128/399 |
| 4,476,862 A | 10/1984 | Pao ......................... 128/303.17 |
| 4,483,338 A | 11/1984 | Bloom et al. .......... 128/303.14 |
| 4,517,965 A | 5/1985 | Ellison ........................ 128/20 |
| 4,517,975 A | 5/1985 | Garito et al. .......... 128/303.13 |
| 4,590,934 A | 5/1986 | Malis et al. ........... 128/303.14 |
| 4,593,691 A | 6/1986 | Lindstrom et al. ..... 128/303.14 |
| 4,597,379 A | 7/1986 | Kihn et al. ................. 128/1 R |
| 4,601,705 A | 7/1986 | McCoy ........................ 604/94 |
| 4,651,734 A | 3/1987 | Doss et al. ............. 128/303.14 |
| 4,811,733 A | 3/1989 | Borsanyi et al. ....... 128/303.14 |
| 4,815,462 A | 3/1989 | Clark ........................ 128/305 |
| 4,838,859 A | 6/1989 | Strassmann ................. 604/95 |
| 4,846,175 A | 7/1989 | Frimberger ............ 128/303.15 |
| 4,873,976 A | 10/1989 | Schreiber ................. 128/334 R |
| 4,894,063 A | 1/1990 | Nashef ........................ 623/13 |
| 4,895,148 A | 1/1990 | Bays et al. ................. 606/213 |
| 4,907,585 A | 3/1990 | Schachar ...................... 606/28 |
| 4,907,589 A | 3/1990 | Cosman ........................ 606/34 |
| 4,924,865 A | 5/1990 | Bays et al. ................... 606/77 |
| 4,927,420 A | 5/1990 | Newkirk et al. |
| 4,944,727 A | 7/1990 | McCoy ........................ 604/95 |
| 4,950,234 A | 8/1990 | Fujioka et al. ................ 604/60 |
| 4,955,882 A | 9/1990 | Hakky .......................... 606/14 |
| 4,966,597 A | 10/1990 | Cosman ........................ 606/50 |
| 4,976,709 A | 12/1990 | Sand ............................ 606/5 |
| 4,976,715 A | 12/1990 | Bays et al. ................... 606/77 |
| 4,998,933 A | 3/1991 | Eggers et al. ................ 606/41 |
| 5,007,908 A | 4/1991 | Rydell ......................... 606/47 |
| 5,009,656 A | 4/1991 | Reimels ....................... 606/48 |
| 5,085,657 A | 2/1992 | Ben-Simhon ................ 606/42 |
| 5,085,659 A | 2/1992 | Rydell ......................... 606/47 |
| 5,098,430 A | 3/1992 | Fleenor ........................ 606/42 |
| 5,100,402 A | 3/1992 | Fan .............................. 606/41 |
| 5,103,804 A | 4/1992 | Abele et al. ................... 128/4 |
| 5,114,402 A | 5/1992 | McCoy ........................ 604/95 |
| 5,152,748 A | 10/1992 | Chastagner ................... 604/95 |
| 5,178,620 A | 1/1993 | Eggers et al. ................ 606/41 |
| 5,186,181 A | 2/1993 | Franconi et al. ............ 128/804 |
| 5,191,883 A | 3/1993 | Lennox et al. .............. 128/401 |
| 5,192,267 A | 3/1993 | Shapira et al. ............... 604/22 |
| 5,201,729 A | 4/1993 | Hertzmann et al. ............ 606/2 |
| 5,201,730 A | 4/1993 | Easley et al. .................. 606/4 |
| 5,201,731 A | 4/1993 | Hakky .......................... 606/15 |
| 5,213,097 A | 5/1993 | Zeindler ..................... 128/401 |
| 5,230,334 A | 7/1993 | Klopotek .................... 128/399 |
| 5,242,439 A | 9/1993 | Larsen et al. ................. 606/15 |
| 5,242,441 A | 9/1993 | Avitall ......................... 606/41 |
| 5,261,906 A | 11/1993 | Pennino et al. .............. 606/46 |
| 5,267,994 A | 12/1993 | Gentelia et al. .............. 606/15 |
| 5,275,151 A | 1/1994 | Shockey et al. ............... 128/4 |
| 5,277,696 A | 1/1994 | Hagen |
| 5,279,559 A | 1/1994 | Barr ............................. 604/95 |
| 5,281,218 A | 1/1994 | Imran |
| 5,284,479 A | 2/1994 | de Jong ....................... 604/60 |
| 5,304,169 A | 4/1994 | Sand ............................ 606/5 |
| 5,308,311 A | 5/1994 | Eggers et al. ................ 606/28 |
| 5,311,858 A | 5/1994 | Adair ............................ 128/4 |
| 5,320,115 A | 6/1994 | Kenna ....................... 128/898 |
| 5,323,778 A | 6/1994 | Kandarpa et al. ........ 128/653.2 |
| 5,334,193 A | 8/1994 | Nardella ...................... 606/41 |
| 5,342,357 A | 8/1994 | Nardella ...................... 606/40 |
| 5,348,554 A | 9/1994 | Imran et al. .................. 606/41 |
| 5,352,868 A | 10/1994 | Denen et al. ................ 219/501 |
| 5,354,331 A | 10/1994 | Schachar ....................... 623/4 |
| 5,364,395 A | 11/1994 | West, Jr. ...................... 606/46 |
| 5,366,443 A | 11/1994 | Eggers et al. .............. 604/114 |
| 5,366,490 A | 11/1994 | Edwards et al. ............. 607/99 |
| 5,382,247 A | 1/1995 | Cimino et al. ................ 606/33 |
| 5,397,304 A | 3/1995 | Truckai ........................ 604/95 |
| 5,401,272 A | 3/1995 | Perkins ........................ 606/15 |
| 5,415,633 A | 5/1995 | Lazarus et al. ............... 604/95 |
| 5,423,806 A | 6/1995 | Dale et al. .................... 606/15 |
| 5,433,739 A | 7/1995 | Sluijter et al. ................ 607/99 |
| 5,437,661 A | 8/1995 | Rieser .......................... 606/15 |
| 5,437,662 A | 8/1995 | Nardella ...................... 606/40 |
| 5,451,223 A | 9/1995 | Ben-Simhon ................ 606/42 |
| 5,458,596 A | 10/1995 | Lax et al. ..................... 606/31 |
| 5,464,023 A * | 11/1995 | Viera .......................... 606/114 |
| 5,465,737 A | 11/1995 | Schachar .................... 128/898 |
| 5,484,403 A | 1/1996 | Yoakum et al. ............... 604/59 |
| 5,484,432 A | 1/1996 | Sand ............................ 606/5 |
| 5,484,435 A | 1/1996 | Fleenor et al. ............... 606/46 |
| 5,487,757 A | 1/1996 | Truckai et al. .............. 607/122 |
| 5,498,258 A | 3/1996 | Hakky et al. ................. 606/15 |
| 5,500,012 A | 3/1996 | Brucker et al. ............. 607/122 |
| 5,507,812 A | 4/1996 | Moore ......................... 623/13 |
| 5,514,130 A | 5/1996 | Baker .......................... 606/41 |

| | | | | |
|---|---|---|---|---|
| 5,524,338 | A | 6/1996 | Martyniuk et al. | 29/825 |
| 5,527,331 | A | 6/1996 | Kresch et al. | 606/170 |
| 5,542,920 | A | 8/1996 | Cherif Cheikh | 604/57 |
| 5,569,242 | A | 10/1996 | Lax et al. | 606/42 |
| 5,599,295 | A | 2/1997 | Rosen et al. | 606/41 |
| 5,630,839 | A | 5/1997 | Corbett, III et al. | 607/137 |
| 5,643,255 | A | 7/1997 | Organ | |
| 5,681,282 | A | 10/1997 | Eggers et al. | 604/114 |
| 5,683,366 | A | 11/1997 | Eggers et al. | 604/114 |
| 5,688,270 | A | 11/1997 | Yates et al. | 606/51 |
| 5,697,909 | A | 12/1997 | Eggers et al. | 604/114 |
| 5,718,702 | A | 2/1998 | Edwards | 606/41 |
| 5,782,795 | A | 7/1998 | Bays | 606/22 |
| 5,810,809 | A | 9/1998 | Rydell | 606/49 |
| 5,897,553 | A * | 4/1999 | Mulier et al. | 606/41 |
| 6,113,591 | A * | 9/2000 | Whayne et al. | 606/34 |
| 6,135,999 | A | 10/2000 | Fanton et al. | |
| 6,277,112 | B1 * | 8/2001 | Underwood et al. | 606/32 |
| 6,379,350 | B1 * | 4/2002 | Sharkey et al. | 606/41 |

FOREIGN PATENT DOCUMENTS

| | | | | |
|---|---|---|---|---|
| EP | 0 479 482 A1 | 4/1992 | | A61B/17/39 |
| EP | 0 521 595 A2 | 1/1993 | | A61M/25/01 |
| EP | 0 572 131 A1 | 1/1993 | | A61B/17/39 |
| EP | 0 542 412 A1 | 5/1993 | | A61B/17/39 |
| EP | 0 558 297 A2 | 9/1993 | | A61M/25/00 |
| EP | 0 566 450 A1 | 10/1993 | | A61N/5/02 |
| EP | 0 682 910 A1 | 11/1995 | | A61B/1/00 |
| EP | 0 479 482 B1 | 5/1996 | | A61B/17/39 |
| EP | 0 729 730 A1 | 9/1996 | | A61B/17/32 |
| EP | 0 737 487 A2 | 10/1996 | | A61M/25/01 |
| EP | 0 783 903 A1 | 7/1997 | | A61N/5/04 |
| FR | 1122634 | 9/1956 | | A61F/19/00 |
| FR | 2 645 008 | 3/1989 | | A61B/17/32 |
| FR | 2 645 008 | 10/1990 | | A61B/17/32 |
| GB | 1 340 451 | 12/1973 | | A61F/1/00 |
| GB | 2160102 A | 12/1985 | | |
| GB | 2 164 473 A | 3/1986 | | A61B/17/36 |
| JP | 5-42166 | 5/1993 | | A61B/17/39 |
| SU | 637118 | 12/1978 | | A61B/17/18 |
| WO | WO 82/02488 | 8/1982 | | A61B/17/39 |
| WO | WO 85/02762 | 4/1985 | | A61B/17/36 |
| WO | WO 92/05828 | 4/1992 | | A61M/25/00 |
| WO | WO 92/10142 | 6/1992 | | A61B/17/36 |
| WO | WO 93/01774 | 4/1993 | | A61F/7/12 |
| WO | WO 93/16648 | 9/1993 | | A61B/17/32 |
| WO | WO 93/20984 | 10/1993 | | B26D/1/11 |
| WO | WO 95/01814 | 1/1995 | | A61N/5/02 |
| WO | WO 95/20360 | 3/1995 | | A61B/17/39 |
| WO | WO 95/10981 | 4/1995 | | A61B/8/12 |
| WO | WO 95/13113 | 5/1995 | | A61N/5/02 |
| WO | WO 95/18575 | 7/1995 | | A61B/17/39 |
| WO | WO 95/25471 | 9/1995 | | A61B/17/39 |
| WO | WO 95/30373 | 11/1995 | | A61B/17/00 |
| WO | WO 95/30377 | 11/1995 | | A61B/17/39 |
| WO | WO 95/34259 | 12/1995 | | A61F/5/48 |
| WO | WO 96/11638 | 4/1996 | | A61B/17/32 |
| WO | WO 96/32051 | 10/1996 | | A61B/1/00 |
| WO | WO 96/32885 | 10/1996 | | A61B/5/04 |
| WO | WO 96/34559 | 11/1996 | | A61B/5/04 |
| WO | WO 96/34568 A | 11/1996 | | A61B/17/36 |
| WO | WO 96/34571 | 11/1996 | | A61B/17/39 |
| WO | WO 96/39914 | 12/1996 | | A61B/1/00 |
| WO | WO 97/06855 | 2/1997 | | A61N/1/40 |
| WO | WO 98/07468 | 2/1998 | | A61N/1/40 |
| WO | WO 98/17190 | 4/1998 | | A61B/18/00 |

OTHER PUBLICATIONS

Houpt, J. et al., "Experimental Study of Temperature Distributions and Thermal Transport During Radiofrequency Current Therapy of the Intervertebral Disc", Spine, vol. 21, No. 15, (1996), pp. 1808–1813.

Troussier, B. et al., "Percutaneous Intradiscal Radio–Frequency Thermocoagulation: A Cadaveric Study", Spine, vol. 20, No. 15, (Aug. 1995), pp. 1713–1718.

Beadling, L., "Bi–Polar electrosurgical devices: Sculpting the future of arthroscopy", Orthopedics today, vol. 17, No. 1, Jan. 1974, 4 pages.

Trimedyne, The Less Invasive Laser Advantage, Omni Spinal Introduction, System.

PRNewswire (Dec. 12, 1994), Two Physicians Perform First Outpatient Cervical Disc Procedure Using Laser Technology.

Introduction to the LDD Disc Kit, Oct. 16, 1996.

Mayer et al., Lasers in Percutaneous Disc Surgery: Beneficial Technology or Gimmick?, vol. 25, No.251, (1993) pp. 38–44.

Schatz et al., Preliminary Experience With Percutaneous Laser Disc Decompression in the Treatment of Sciatica, vol. 38 No. 5, Oct. 1995, pp. 432–436.

Savitz M. A., Same–day Microsurgical Arthroscopic lateral–approach Laser–assisted (SMALL) Fluoroscopic Discectomy, vol. 80, Jun. 1994 pp. 1039–1045.

Sluijter M.E., The Use of Radiofrequency lesions For Pain Relief in Failed Back Patients, vol. 10 No. 1 (1988).

Cosman et al., Theoretical Aspects of Radiofrequency lesions in the Dorsal Root Entry Zone, vol. 15 No. 6 (1984) pp. 945–950.

Wilkins et al., Neurosurgery: Method of Making Nervous System Lesions, ch. 337, pp. 2490–2499.

Yonezawa et al., The System and Procedure of percutaneous Intradiscal Laser Nucleotomy, vol. 15, No.5 (1990) pp. 1175–1185.

Kolarik et al., Photonucleolysis of Intervertebral Disc and it's Herniation, (1990).

Gottlob et al.,Lasers in Surgery and Medicine: Holmium:YAG Laser Ablation of Human Intervertebral Disc: Preliminary Evaluation, vol. 12, (1991) pp. 86–91.

Buchelt et al., Lasers in Surgery and Medicine:Fluorescence Guided Excimer Laser Ablation of Intervertebral Discs In Vitro, vol. 11, (1991) pp. 280–286.

Choy et al., Percutaneous Laser Disc Decompression: A New Therapeutic Modality, vol. 17 No. 8, (1992) pp. 949–956.

Sluijter et al., Persistant Pain, Modern Methods of Treatment: Treatment of Chronic Back and neck Pain, vol. 3, (1981) pp.141–179.

Sluijter, Int Disabil Studies: The use of Radio Frequency Lesions For Pain Relief on Failed Back, vol. 10, Sept. 4, 1996, pp. 37–43.

Shatz et al., CJS JCC Preliminary Experience With Percutaneous Laser Disc Decompression in the Treatment of Sciatica, vol. 38 No. 5, Oct. 1995 pp. 432–436.

Gerber et al., Der Orthopade: Offene Laserchirurgie am Bewegungsapparat, vol. 25, (1996) pp. 56–63.

Gehring W.J., Exploring the Homeobox, (1993), pp. 215–221.

Kelly L.E., Purification and Properties of a 23kDa Ca2+–binding Protein, (1990) 271, pp. 661–666.

Sluyter, Radiofrequency Lesions in the Treatment of Cervical Pain Syndromes, Radionics, Inc. (1989).

Buchelt et al., *Lasers in Surgery and Medicine*:Erb:YAG and Hol:YAG Laser Ablation of Meniscus and Intervertebral Discs, vol. 12 No. 4, (1992) pp. 375–381.

Leu et al., *Der Orthopade*: Endoskopie der Wirbelsaule: Minimal–invasive Therapie, vol. 21, (1992) pp. 267–272.

Phillips et al., JMRI: MR Imaging of Ho: YAG Laser Diskectomy with Histologic Correlation, vol. 3 No. 3, May/Jun. 1993.

Bromm et al., *Human Neurobiology*: Nerve Fibre Discharges, Cerebral Potentials and Sensations Induced by CO2 laser Stimulation, vol.3, (1984) pp.33–40.

Kolarik et al., Photonucleolysis of Intervertebral Disc and it's Herniation, vol. 51, (1990) pp. 69–71.

Vorwerck et al., Laserablation des Nucleus Pulposus: Optische Eigenschaften von Degeneriertem Bandscheibengewebe im Wellenlangenbereich von 200 bis 2200nm, vol. 151 No. 6, (1989) pp. 725–728.

Wolgin et al., Excimer Ablation of Human Intervertebral Disc at 308 Nanometers, vol. 9, (1989) pp. 124–131.

Davis, Early experience with Laser Disc Decompression, vol. 79 No. 1, (1992) j. Florida M.A.

Quigley et al., Laser Discectomy: Comparison of Systems, vol. 19 No. 3 (1994) pp. 319–322.

Mehta et al., The Treatment of Chronic back Pain: A Preliminary survery of the Effect of Radiofrequency Denervation of the Posterior Vertebral Joints, vol. 34 (1979) pp. 768–775.

Patil et al., Percutaneous Discectomy Using the Electromagnetic Field Focusing Probe: A Feasability Study.

McCulloch et al., CMA Journal: Percutaneous Radiofrequency Lumbar Rhizolysis (rhizotomy), vol. 116, Jan. 8, 1977.

Yonezawa et al., The System and Procedure of Percutaneous Intradiscal Laser Nucleotomy, vol. 15 No. 11 (1990).

Sminia et al., Effects of 434 MHz Microwave Hyperthermia applied to the rat in the region of the cervical Spinal Cord, vol. 3 No. 5 (1987) pp. 441–452.

Sluijter et al., Treatment of Chronic Back and Neck Pain by Percutaneous Therman Lesions, vol. 3 (1981.

\* cited by examiner

FIG. 8B

SURGICAL INSTRUMENT WITH OFF-AXIS ELECTRODE

This application claims priority to U.S. Provisional Application No. 60/037,620 filed Feb. 12, 1997, and is a continuation-in-part of U.S. patent application Ser. No. 09/022,688 filed Feb. 12, 1998, now U.S. Pat. No. 6,168,593, the entire contents of each application being incorporated herein by this reference.

BACKGROUND OF THE INVENTION

1. Field of the Invention

This invention is directed to electrodes used in electrosurgical procedures.

2. Description of Related Art

Numerous patents and patent applications exist in the field of electrosurgical methods and apparatuses that describe electrode shapes used to modify tissue in vivo. Early devices, including the design of their electrodes, were crude, and advances in surgical techniques over the years, especially the development of surgery using endoscopes (arthroscopic surgery), have continually led to new designs of electrodes as new uses call for the design of an apparatus specifically designed for that new use. Arthroscopic surgery is becoming increasingly popular, because it generally does less damage than open procedures, produces less scarring in and around joints, and results in faster healing and return of the patient to full productivity.

Nevertheless, arthroscopic surgery has its limitations. The surgeon must operate through a narrow tube formed in the body on which surgery is being carried out, which is awkward. Only one probe can be used at a time for many operations. Often the viewing camera is positioned at an angle different from the surgeon's normal gaze. This contrasts with "open surgery" where the surgeon has relative ease of viewing the surgical site and can freely move both hands, even utilizing the hands of colleagues.

In view of such difficulties of arthroscopic surgery, it is understandable that radiofrequency (RF) probes which simultaneously cut and coagulate are preferred. However, current RF probes are poorly adapted to certain activities, such as smoothing surfaces located at an angle to the axis of entry of an arthroscopic probe.

Current probes have convex, pointed and/or flat tips and are generally oriented so that the ablation process occurs substantially along the axis of the elongated probe being used for the operation. U.S. Pat. No. 5,308,311 (issued May 3, 1994 to Eggers and Shaw) is exemplary in that it has a pointed tip with a convex side. With current probes, the surgeon has poor ability to ablate tissue in directions off the axis of insertion of the probe and little control when attempting to ablate a tough substrate, such as cartilage. Thus, there are certain procedures that surgeons still prefer to perform in the "open." Unfortunately, this often results in bigger scars, longer convalescence, and more irritation of an already irritated joint.

What is needed is a probe that can direct ablation of tissue at an angle to the principal axis of the probe, as well as a technique for easy manufacture of such an apparatus. Some procedures which have been considered too awkward or difficult to perform by arthroscopy can then be performed efficiently by arthroscopy.

SUMMARY OF THE INVENTION

It is an object of the invention to provide an electrode for an electrosurgical apparatus capable of superior performance in ablating collagen, including collagen present in cartilage, relative to existing electrodes.

It is a further object of the invention to provide an electrode for an electrosurgical apparatus that can ablate tissue at an angle to the principal axis of the probe on which it is used without requiring a bend in the probe itself.

It is another object of the invention to provide an electrode for an electrosurgical apparatus that can be adapted to multiple end uses by a single selection of a mechanical operation on different locations on the electrode surface during manufacture of the electrode.

These and other objects of the invention as will hereinafter become more readily apparent have been accomplished by providing an electrosurgical electrode, comprising a metal conductor having a first external surface area and having a convex body, a flat face on the body, and a connector for attaching the body to an electrosurgical probe handle, and an insulating layer covering the first external surface of the metal conductor except at a selected second area of one of the convex body and the flat face, the second area being positioned on the metal conductor so that a line from a geometric center of the second area and substantially perpendicular to the second area intersects at an angle an axis formed by a probe handle and the metal conductor upon attachment of a probe handle to the connector, wherein the second area is less than 30% of the first area.

The electrode is used in preferred embodiments in an electrosurgical probe, comprising a handle, an elongated probe neck connected to the handle and having a terminus distal to the handle, and the electrode of the invention located at the terminus of the elongated probe neck. The electrosurgical probe so formed is preferably used as part of an electrosurgical system, comprising an electrical power supply, a first electrode adapted to contact and electrically ground a living body, the first electrode being electrically connected to the power supply, and an electrosurgical probe, the probe comprising a handle, an elongated probe neck connected to the handle and having a terminus at a distal end from the handle, and a second electrode, the second electrode being the electrode of the invention and being located at the terminus of the elongated probe neck, the probe being adapted to contact the body and complete an electrical circuit, the second electrode being electrically connected to the power supply.

Also provided is a general method of manufacturing off-axis electrosurgical electrodes, by preparing a metal conductor having a first external surface area and having a first body shape and a connector for attaching the body to an electrosurgical probe handle, applying an insulating layer to cover all of the first external surface of the metal conductor, and removing a portion of the insulating layer at a selected second area of the body shape, the second area being positioned on the metal conductor so that a line from a geometric center of the second area and substantially perpendicular to the second area intersects the principal axis of the probe at an angle, the axis being defined by the probe handle and the metal conductor upon attachment of a probe handle to the connector, generally through an elongated linear neck. Any electrode so formed is also part of the present invention.

In another embodiment of the invention a surgical instrument is disclosed. The surgical instrument includes a handle, an elongated probe and at least one electrode. The elongated probe is connected to the handle. The elongated probe has a terminus distal to the handle. The electrode includes an electrode surface positioned on the terminus so that a line from a geometric center of the electrode surface and substantially perpendicular to the electrode surface intersects at an angle a longitudinal axis formed by the elongated probe. The conductor attaches the electrode to the handle.

In a further embodiment of the invention an apparatus for electrosurgical treatment of a body is disclosed. The apparatus comprises an elongated probe member having proximal and distal extremities, a handle connected to the proximal extremity and an electrode carried by the distal extremity, the probe member including a shaft having proximal and distal ends and a distal opening, the electrode including a flat plate and a cap, the plate being fixed to the distal end of the shaft and at least partially covering the distal opening, the cap enclosing the plate and a portion of the distal end of the shaft.

BRIEF DESCRIPTION OF THE DRAWINGS

The present invention now being generally described, the same will become better understood by reference to the drawings that form part of this specification, wherein.

DESCRIPTION OF THE PREFERRED EMBODIMENTS

The invention comprises improved electrodes used for electrosurgical operations, an apparatus incorporating such electrodes, and a general method for making an off-axis electrode useful for arthroscopic surgery. The electrosurgical electrode, in its preferred embodiments, comprises a metal conductor having a first external surface area and having a convex body, a flat face on the body, and a connector for attaching the body to an electrosurgical probe handle. This preferred electrode shape will be used to describe preparation of an electrode of the invention, but those skilled in the arts of making and manipulating solid metal bodies will recognize that other shapes can be manufactured in a similar manner. The preferred electrode bodies can readily be formed from a spherical metal body blank by grinding one region with a flat grinding element to produce a flat face, before or after drilling (or otherwise providing) a location to attach the electrode to an elongated probe.

Instead of providing a pencil-eraser-like electrode at the terminus of the probe, so that cutting or ablation operations occur primarily at the tip of and collinearly with the principal axis of the probe, an insulating layer covering the first external surface of the metal conductor is provided except at a selected second area of one of the convex body and the flat face. The area is positioned on the metal conductor so that a line from the geometric center of the second area and substantially perpendicular to the second area intersects at an angle an axis defined by a line between a probe handle and the metal conductor upon attachment of a probe handle to the connector. In preferred embodiments, the angle is greater than 60°; in more preferred embodiments, greater than 80°. The second area is sufficiently small so that none of the second area is intersected by the principal axis of the probe. Typically, the second area is less than 30% of the first area, preferably less than 20%.

Selection of materials to use in manufacturing an electrode of the invention (which are primarily the metal used in the body of the electrode and the insulator used to cover the metal) can be made from any of the materials normally used in the art of electrosurgical electrode manufacture. Biocompatibility and stability in the presence of heat are primary factors in the choice of both metals and insulating layers. For preferred embodiments of the invention, metals include stainless steel, gold, silver, and platinum; insulating materials include polytetrafluoroethylene (e.g., Teflon) and nylon. A typical electrode will be prepared from a metal electrode having a tensile strength of 25 to 400 ksi, a thermal conductivity of 0.025 to 1.0 ca/cm$^2$/cm/s/° C., a resistivity of 80 to 1500 Ωm, and an EMF of −0.44 to +1.5 V.

For indications in which high power output through the electrode is desired, such as in the ablation of cartilage, small active electrode areas are desired in order to have high current densities. For such uses, the exposed electrode area typically has a surface area of from 0.005 to 0.150 square inches, preferably from 0.010 to 0.080 square inches for treatment of chondromalacia, and from 0.015 to 0.020 square inches for ablation. For exposed electrode areas of these sizes, a 50-watt RF power supply provides satisfactory cartilage ablation.

Probes containing electrodes of the invention can have any of the features present in other probes, such as thermocouples or other sensing devices for use in feedback control of the power supply. Electrodes in which the body has a hollow interior (to allow room for such thermocouples, for example) are preferred when appropriate for the intended end use of the electrode.

An electrosurgical probe of the invention will have a handle, an elongated probe neck connected to the handle and having a terminus distal to the handle, and the electrode of the invention located at the terminus of the elongated probe neck. Any other device incorporating an electrode of the invention falls within the scope of the invention. For example, an electrosurgical system of the invention will have an electrical power supply, a first electrode adapted to contact and electrically ground a living body, the first electrode being electrically connected to the power supply, and an electrosurgical probe of the invention, which will in turn incorporate the electrode of the invention, that electrode being electrically connected to the power supply to complete the circuit. Preferred are radio frequency energy power supplies, although the electrodes of the invention can be used with other power supplies, such as microwave power supplies. Systems in which the power supply is operably connected to a temperature-sensitive feedback monitor located in the probe are preferred, such as those described in U.S. applications Ser. Nos. 08/637,095 and 08/714,987. These applications also contain many details related to other components that can be used with the electrodes of the present invention.

In all of these operations, current and voltage are used to calculate impedance. An operator-set level of power and temperature may be determined, and this level can be maintained manually or automatically if desired. The amount of RF energy delivered controls the amount of power. Feedback can be the measurement of impedance or temperature and occurs either at the controller or at the RF source if it incorporates a controller. Impedance measurement can be achieved by supplying a small amount of nontherapeutic RF energy. Voltage and current are then measured to confirm electrical contact. Accordingly, it is well within the skill of the art to determine satisfactory optimum operating conditions for electrodes of the invention having different active electrode areas from those exemplified herein. Circuitry, software and feedback to a controller result in full process control and are used to change (i) power (modulate)—including RF, incoherent light, microwave, ultrasound and the like, (ii) the duty cycle (on-off and wattage), (iii) monopolar or bipolar energy delivery, (iv) fluid (electrolytic solution) delivery, flow rate and pressure and (v) determine when ablation is completed through time, temperature and/or impedance.

The present invention provides a general method of manufacturing off-axis electrosurgical electrodes, by preparing a metal conductor having a first external surface area and having a first body shape and a connector for attaching the body to an electrosurgical probe handle, applying an insulating layer to cover all of the first external surface of the metal conductor, and removing a portion of the insulating layer at a selected second area of body shape, the second area being positioned on the metal conductor so that a line from a geometric center of the second area and substantially perpendicular to the second area intersects the principal axis of the probe at an angle, the axis being defined by the probe handle and the metal conductor upon attachment of a probe handle to the connector, generally through an elongated linear neck. Since the body of the electrode is formed from metal that is harder than the insulators commonly used in such electrodes, a grinding process can be used to remove a selected portion of an initially applied layer that covers the entire external surface of the electrode body. Care may need to be taken with softer metals if their original shape is to be maintained, but selection of grinding conditions based on the hardness of the material being removed are well know in the grinding art. In an embodiment of the invention insulating material on a flat surface is readily removed using a grinding disk; if desired a flat face can be formed on the electrode at the same time by using a grinding material harder than both the insulator and the metal used in the disk. Such a technique is particularly useful with softer metals, such as gold. Insulating material on a convex surface can be removed by a wire brush or a specially shaped grinding wheel. In another embodiment the probe surface can be masked in the tip region. Insulation material can then be applied to the probe. The mask is then removed exposing the conductive tip. Any electrode formed by the manufacturing process described here is also part of the present invention.

Figure 1A:
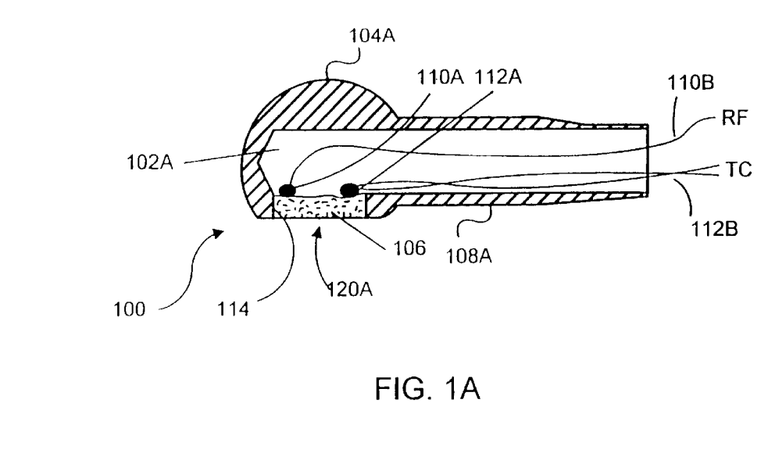
FIGS. 1A–C show alternate views of an embodiment of an off-axis RF tool tip.
Figure 1B:
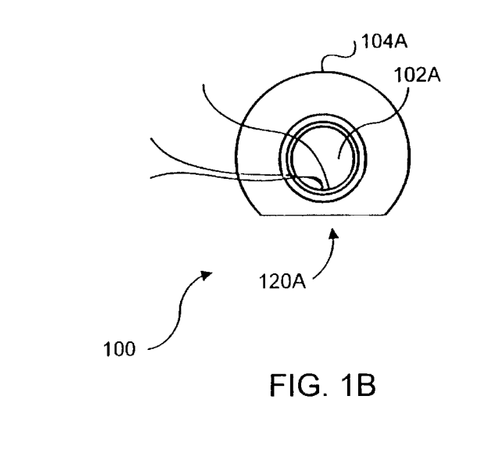
Figure 1C:
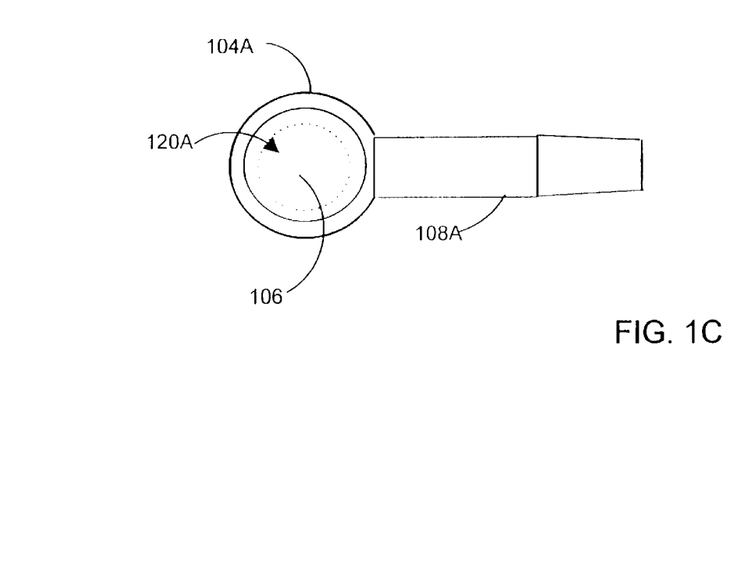

Turning now to the drawings, FIGS. 1A–C, 2A–C show alternate embodiments of a detachable tip with an off-axis electrode. In the embodiments shown in FIGS. 1A–C the detachable tip may be made from a generally insulating material. In the embodiment shown in FIGS. 2A–C the detachable tip may be made from a generally conductive material. FIGS. 1A–C show, respectively, a cross-sectional elevation, an end view and an exterior view of the detachable tip. As shown in FIG. 1A, the detachable tip 100 includes a tapered shaft 108A connected to an arcuate extension 104A. A flat electrode surface 120A is defined at the terminus of the arcuate extension. The electrode's surface is located about a normal axis which is orthogonal to the axis of the tapered shaft 108A. As shown in FIG. 1A, an annular cavity 102A is defined by both the tapered shaft and arcuate extension. The flat surface 120A defines a through hole 114 which connects to the annular cavity 102A. A conductive material 106 fills the through hole. In an embodiment of the invention the conductive material comprises silver solder, or conductive powdered metal. RF power is provided to the tip through a wire 110B which is joined at 110A to the conductive material 106. To provide feedback for control of RF power, a thermal couple 112A is also bonded to the conductive material. Lead wires 112B extend from the thermal couple to an exit point at a proximal end of the tapered shaft.

Figure 2A:
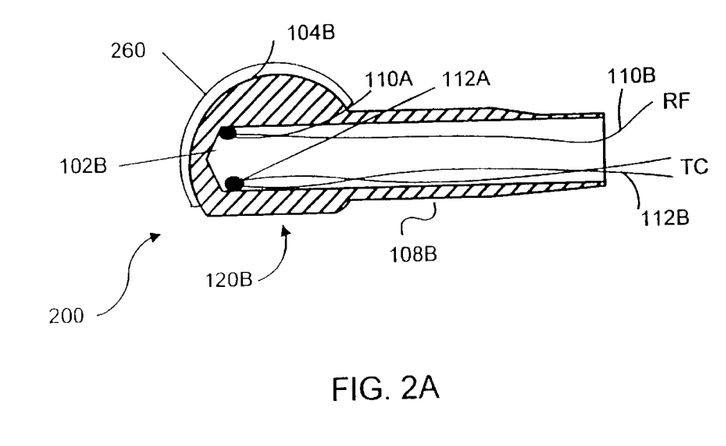
FIGS. 2A–C show another embodiment of an off-axis tool tip for RF surgical instruments.
Figure 2B:
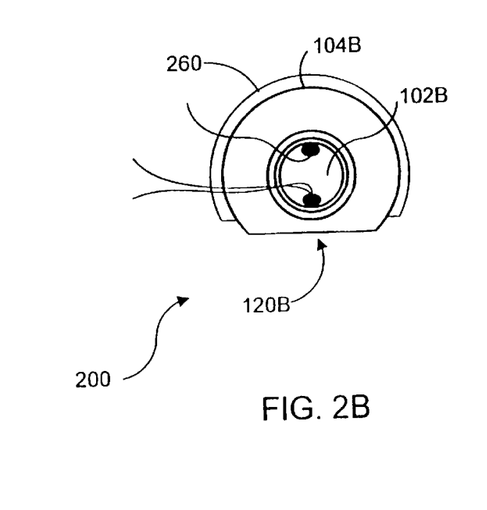
Figure 2C:
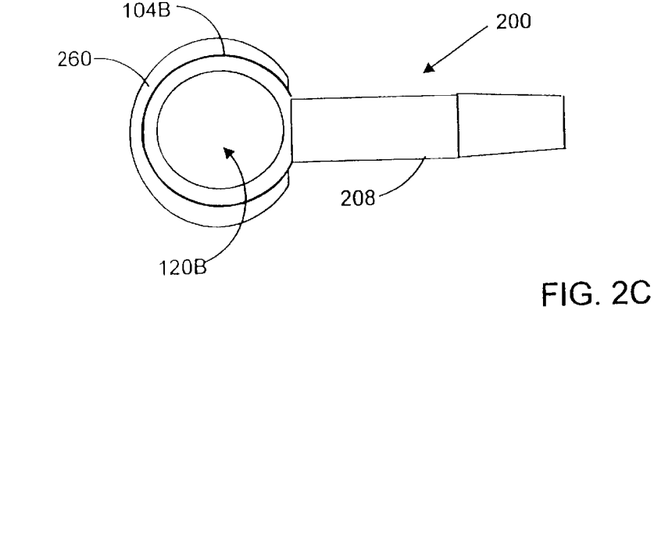

FIGS. 2A–C show an alternate embodiment of the detachable tip to that discussed above in connection with FIGS. 1A–C. In this embodiment the entire detachable tip 200 may be comprised of a conductive material. An annular cavity 102B is defined within both the tapered shaft 108B and the arcuate extension 104B of the detachable tip. At a terminus of the arcuate extension a flat surface 120B is defined. Portions of the arcuate extension are covered with insulator 260 so as to localize the RF generation to flat surface 120B. Within the annular cavity 102B of the generally conducting detachable tip 200, both the RF and thermal couple connections are made. Because the detachable tip is generally conducting, no through hole to the flat surface 120B is required. Instead, thermal couple 112A is bonded to an interior surface of the annular cavity and wires 112B to that thermal couple extend from the distal end of the tapered shaft 108B. The RF wire 110B terminates in a bond 110A to the interior surface of the annular cavity.

In the embodiments shown the electrode portion of the detachable tip provides monopolar RF delivery which induces tissue heating by a combination of molecular friction and conduction. A complete electrical circuit for monopolar RF delivery includes a return current pad in electrically conductive contact with the patient's body. The pad in turn is connected to the RF generator to complete an electrical circuit from the RF delivery 110 within the detachable tip through the conductive tissue to the return pad. This will be obvious to those skilled in the art. Bipolar delivery can be implemented using the teachings of the current invention by providing at least two distinct electrodes on the tip, each connected to outgoing and return electrical paths from the RF power supply. Monopolar heating has the advantage that tissue, rather than the surgical instrument itself, is heated. In bipolar delivery, energy follows the path of least resistance through conductive irrigating solution in the body tissue, causing superficial surface heating with minimal tissue penetration.

Figure 3A:
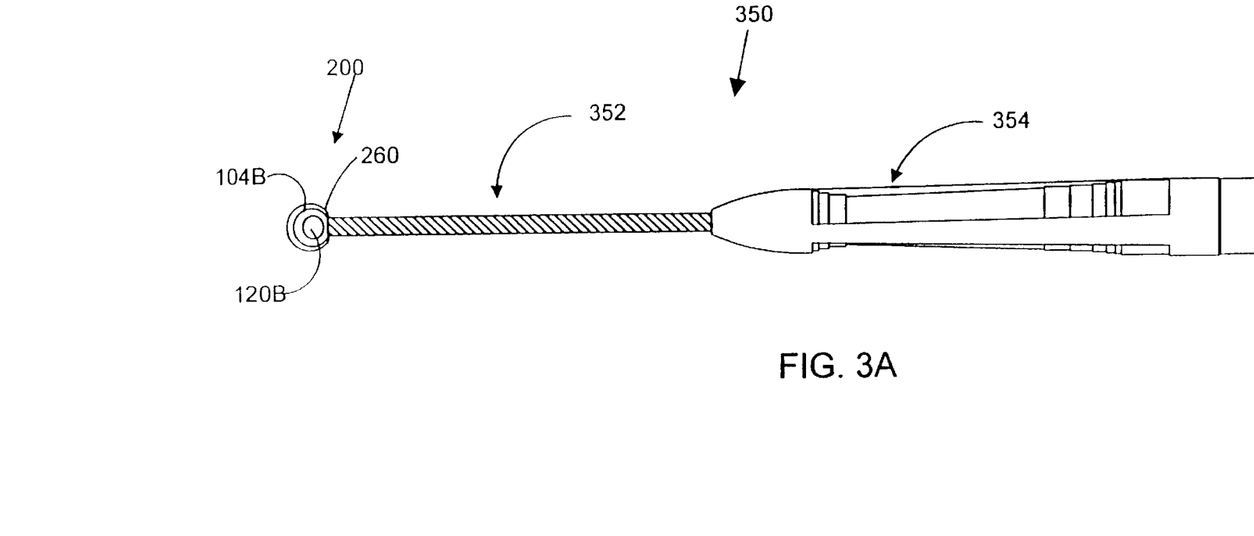
FIGS. 3A–B show the tool tip of FIGS. 2A–C in a surgical instrument.
Figure 3B:
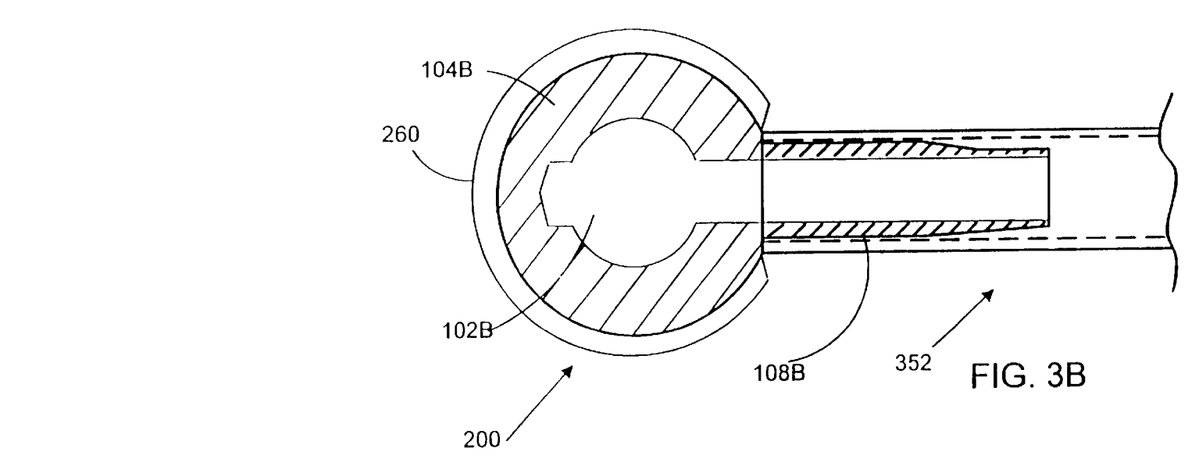
Figure 4A:
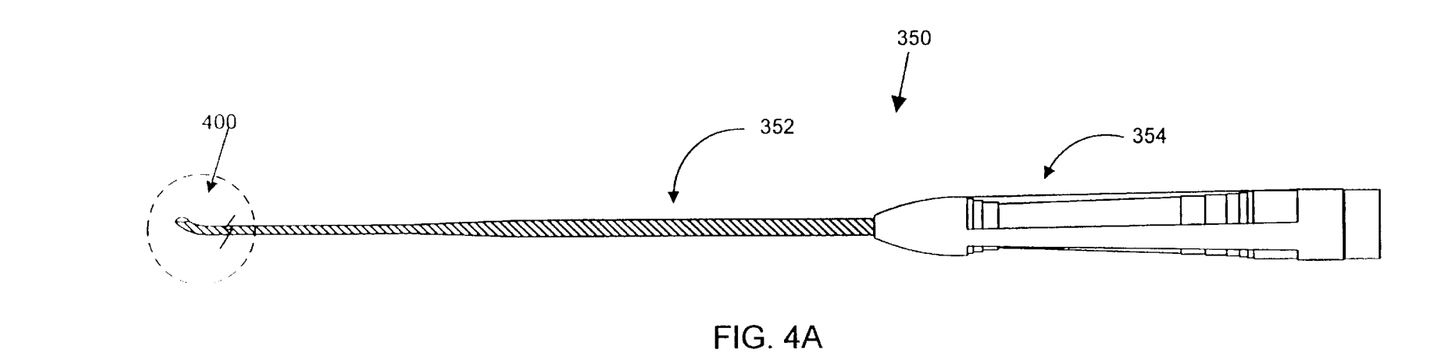
FIGS. 4A–E show a surgical instrument with an integral off-axis tip.
Figure 4B:
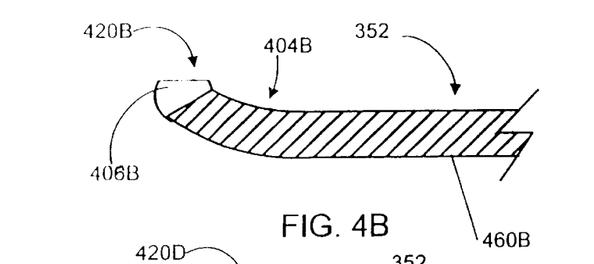
Figure 4C:
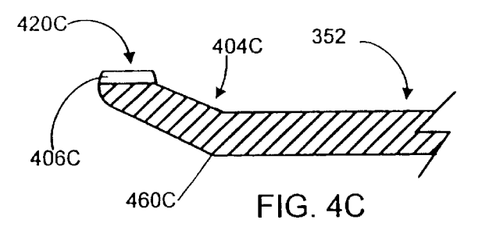
Figure 4D:
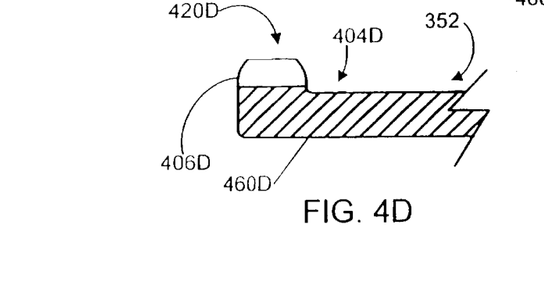
Figure 4E:
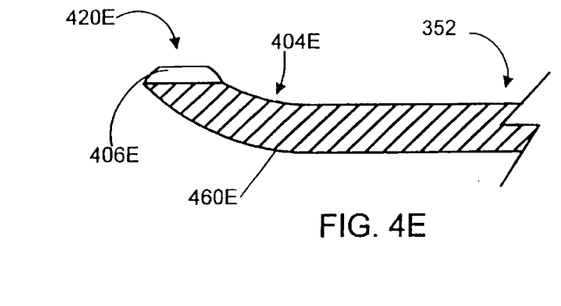

FIGS. 3A–B show the detachable tip assembled with a surgical instrument 350. FIG. 3A shows the surgical instrument to include a handle 354, an extended probe or shaft 352 and the detachable tip 200 at a distal end of the probe 352. The handle is attached to the proximal end of the probe. FIG. 3B shows the detachable tip 200 frictionally affixed within the distal end of probe 352. Probe 352 is tubular in cross-section and has an interior annular surface dimensioned to press fit with the exterior surface of tapered shaft 108B. Thus, the detachable tip is fastened to the distal end of probe 352. In alternate embodiments the tip can be fastened to the shaft by press fit, by mechanical fastener, by an interlocking action, by an adhesive compound, a bonding compound, by braising or by welding, for example. Electrical connections to both the RF and thermal couple connections discussed above in connection with FIGS. 2A–C extend the length of the probe to power and control connections within the handle 354.

FIGS. 4A–E show an alternate embodiment for the off-axis RF tip of the current invention. The tip in these embodiments is integrated with the probe 352. The probe has a distal end 400 on which various embodiments of arcuate extensions 404B–E are shown in, respectively, FIGS. 4B–E. These arcuate extensions can be formed on the distal end of the probe through fabrication steps such as swaying, rotoforming, bending, etc. The probe may be solid or tubular in cross-section. In embodiments where the probe is solid, it may be made of a conductive material coated with an insulator 460B–E. At the terminus of the probe the insulating covering 460B–E ceases and an exposed portion of the probe forms a conductive electrode on the tip. Planar electrode surfaces 420B–E are shown in, respectively, FIGS. 4B–E. RF connection can be made to the probe within the handle. The electric current will be carried the length of the conductive probe and will radiate from the flat surfaces 420 at the exposed probe tip 406B–E also shown respectively in FIGS. 4B–E. In an alternate embodiment of the current invention the probe is annular in cross-section and may be made from an insulating or conductive material. In the event the probe is made from an insulating material, the probe tip 406B–E shown in, respectively, FIGS. 4B–E may be comprised of a conductive material such as silver solder or conductive metallic powder. RF and thermal couple connections may be made to this conductive material 406 through wires extending from the handle through the annular opening within the probe 352 to the conductive tip material 406. The flat surfaces 420B–E may be formed on the tip by grinding and allow radiation of RF energy from an electrode surface whose normal axis is off the longitudinal axis about which the probe 352 is defined.

Figure 5A:
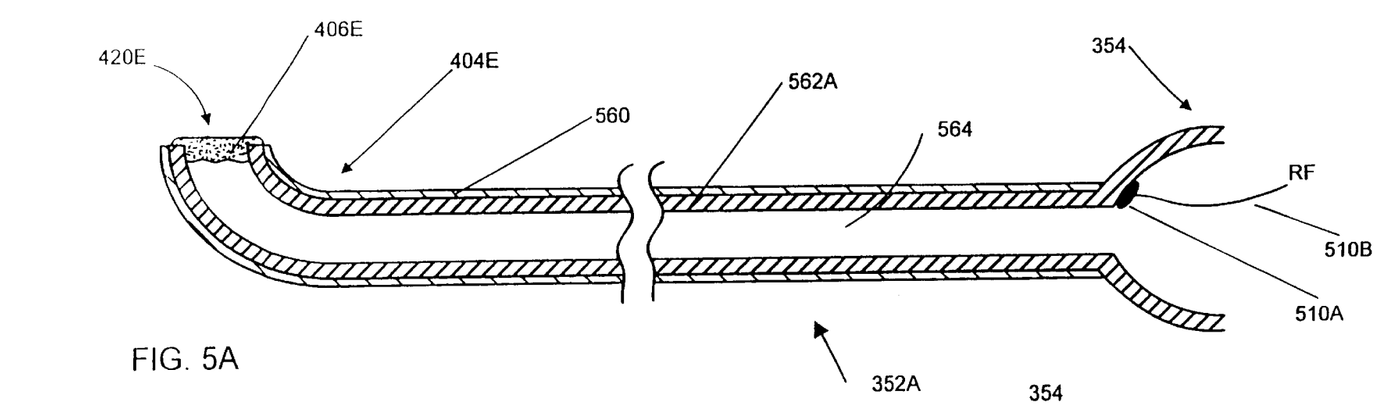
FIGS. 5A–B show cross-sectional views of the surgical tool and tips shown in FIGS. 4A–E.
Figure 5B:
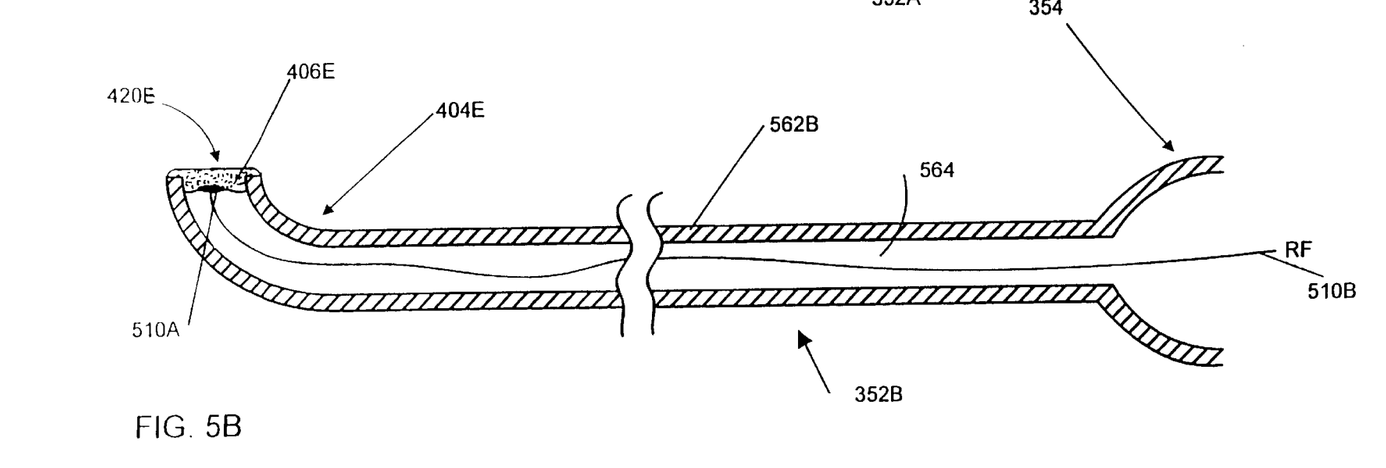

FIGS. 5A–B show cross-sectional views of the integrated off-axis tip discussed above in connection with FIGS. 4A–E. FIG. 5A shows an embodiment in which the probe 352A is fabricated from a conductive material. FIG. 5B shows an embodiment in which probe 352B may be fabricated from an insulating material. The conductive probe 562A shown in FIG. 5A is covered with an insulating material 560. This material covers all portions of the probe with the exception of the distal end. The probe has an arcuate extension 404E. The probe may have an annular cavity 564 in cross-section. In alternate embodiments the probe may be solid in cross-section. At the distal end of the probe, a conductive material 406E fills the annular opening and defines a flat electrode surface 420E. A normal to this surface is in the embodiment shown off-axis or in the embodiment shown orthogonal to the longitudinal axis of the probe 352A. RF power is supplied to the conductive material 406E via the conductive probe 562A from an RF attachment in the handle 354. An RF junction 510A to an RF delivery wire 510B is made to the proximal end of the probe where it joins to handle 354.

In FIG. 5B the probe 562B defines an annular cavity 564 extending from the proximal to the distal end of the probe. At the distal end of the probe an arcuate extension 404E is defined. At the terminus of the probe a conductive material 406E fills the annular opening and defines a flat electrode surface 420E. Because the probe is generally insulating, a connection is made between RF delivery wire 510B, which extends the length of the annular cavity of the probe and forms a junction 510A with the conductive material 406E. Either embodiment shown in FIG. 5A or 5B can additionally include a thermal couple to provide temperature feedback to an RF power source.

Although each of the above mentioned embodiments discloses an electrode surface which is flat it will be obvious to those skilled in the art that other surface profiles including concave and convex may also be utilized for the off-axis electrodes. Choice of surface profile will depend on the surgical environment. For example, in joints a flat electrode surface allows a probe with a low form factor. Additionally, a flat surface allows a larger contact area between the electrode and the surgical site. A concave surface may have the further advantage of isolating the surgical site from surrounding saline solution. The isolation of the concave design allows better thermal conductivity and therefore reduced thermal fluctuation.

Embodiments intended for use in the treatment of chondromalacia preferably have a convex surface with a radius of curvature of from 0.010 to 0.25 inches, preferably from 0.040 to 0.060 inches. For this indication, an electrode formed from a metal body so that the first external surface area described above is essentially the surface of a sphere with one flat face is preferred.

Figure 6:
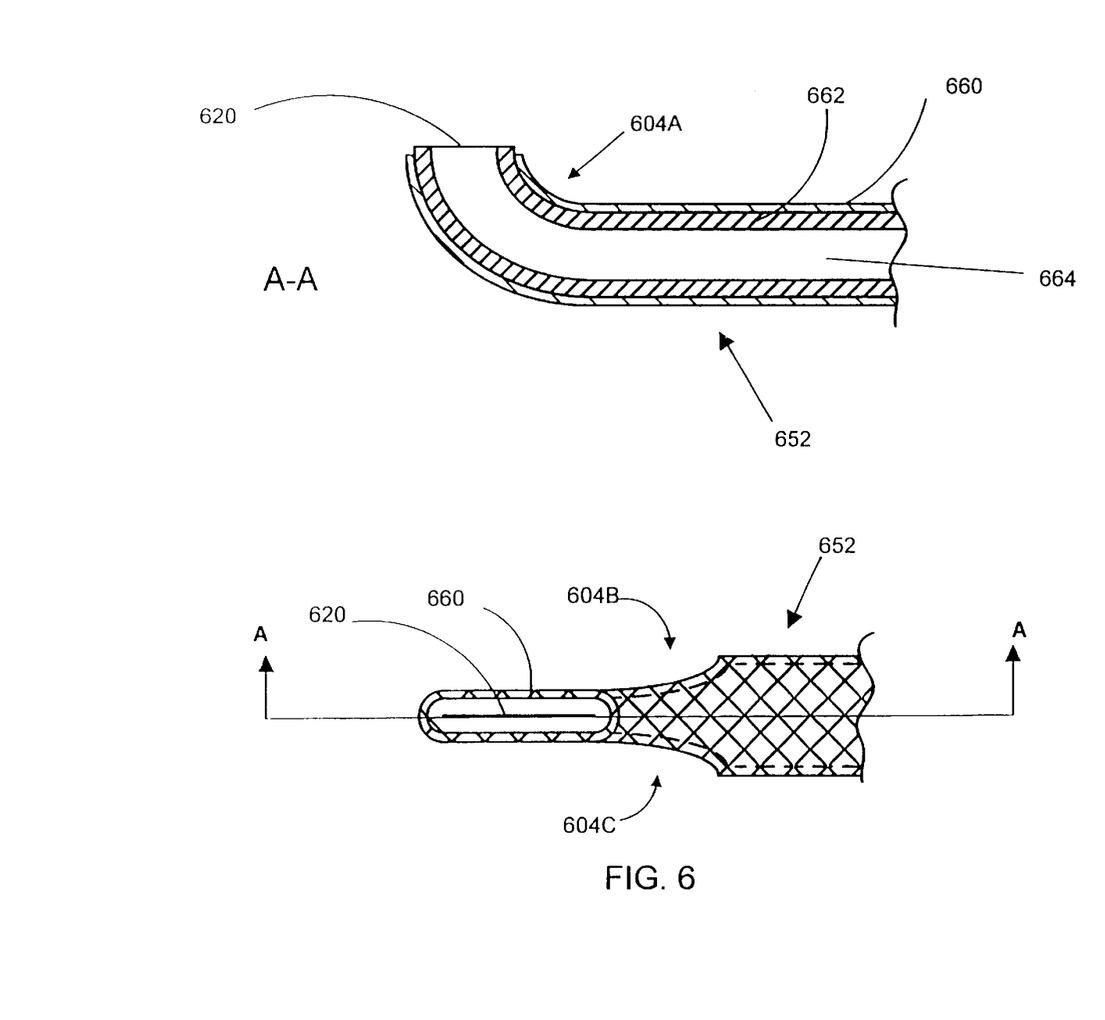
FIGS. 6 and 7A–B show alternate embodiments of the surgical tool with an integral off-axis tip.
Figure 7A:
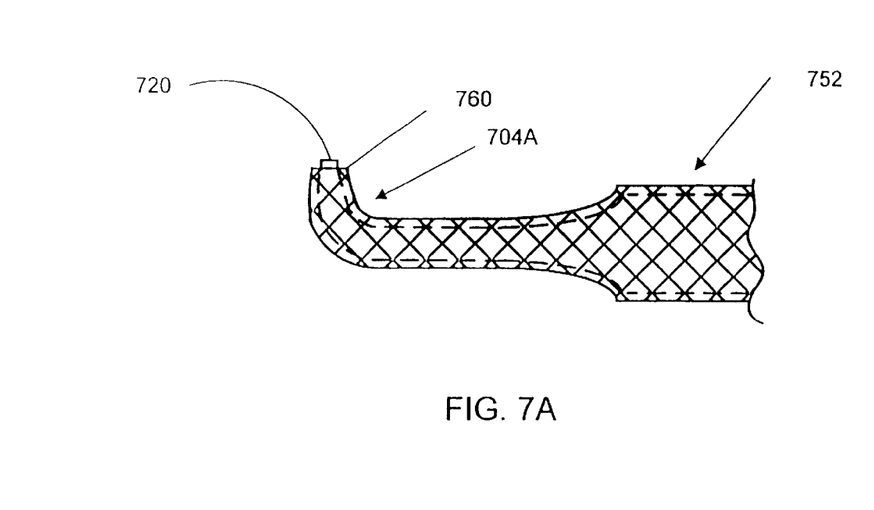
Figure 7B:
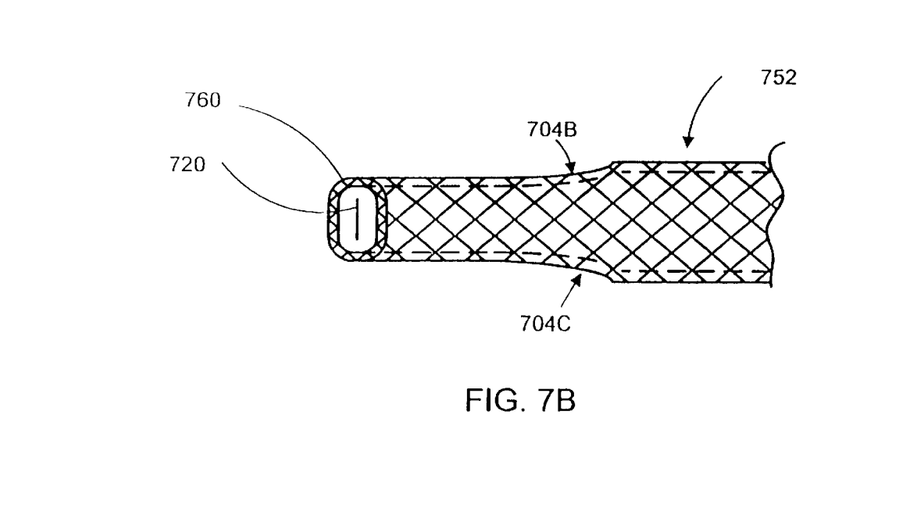

FIGS. 6 and 7A–B show an alternate embodiment to the probes shown in FIGS. 1–5. In these embodiments, the tip itself is formed from the distal end of the probe via machining operations such as swaying, thermal forming, bending, etc. No conductive material is required and no attachable/detachable tip is required. Instead, the terminus of the probe is formed into an off-axis tip. In the embodiment shown in FIG. 6, the probe 652 is made from a conductive material 662 about which an insulating shell 660 is formed. The insulating shell can be formed in a variety of fashions. In one embodiment the insulating shell can be formed by heat shrink tubing which is slipped over the conductive probe and to which heat is applied to cause it to conform to the exterior of the probe. In an alternate embodiment, the probe itself after being formed can be dipped in an insulating solution. In still another embodiment, the probe can be coated with a powdered insulator which is activated by temperature to conform to the exterior surface of the probe. (In one such embodiment, Corvel® nylon coating may be used and is available from Morton Powder Coatings, P.O. Box 15240, Reading, Pa. 19612-5240, (800) 367-3318). In FIG. 6 arcuate surfaces 604B–C are formed on opposing sides of the distal end of the probe. As shown in cross-sectional view A—A, an arcuate extension 604A is also formed at the terminus of the probe, thereby positioning the tip of the probe 620 so as to form a surface the normal to which is off the longitudinal axis about which the probe itself is defined. The tip itself is further formed to pinch or close the opening of annular cavity 664. This has the advantage of forming a longitudinal electrode surface 620 which may, with appropriate shaping operations such as grinding, offer a cutting surface or scraping surface which can be utilized in conjunction with the cutting or cauterizing capability of RF alone.

FIG. 7A shows an alternate embodiment to that shown in FIG. 6 in which a distal end of a probe is formed into an off-axis electrode 720 having a longitudinal electrode surface the normal to which is orthogonal to a longitudinal axis about which the probe is defined. Additionally, in contrast to the embodiment shown in FIG. 6, the electrode surface 720 is rectangular in cross-section and the longitudinal axis of that surface is also orthogonal to the longitudinal probe axis. Appropriate shaping of this surface allows chiseling or scraping of a mechanical nature to complement the RF surgical process. All portions of the probe except for the exposed tip are wrapped in an insulating shell 760. The probe 752 is fabricated with opposing arcuate surfaces 704B–C and an arcuate extension 704A which positions the electrode tip 720 in the manner described and discussed above. The probe may be annular or solid in cross section.

Figure 8A:
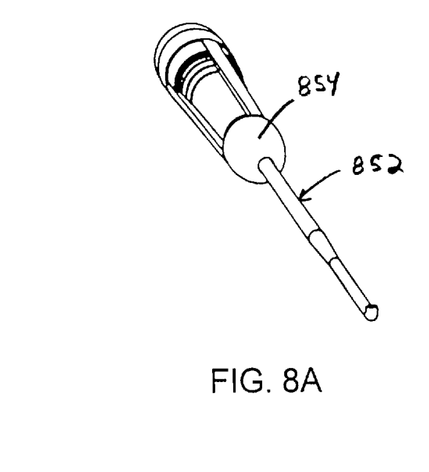
FIGS. 8A–C show a further embodiment of the surgical tool with an off-axis tip.
Figure 8B:
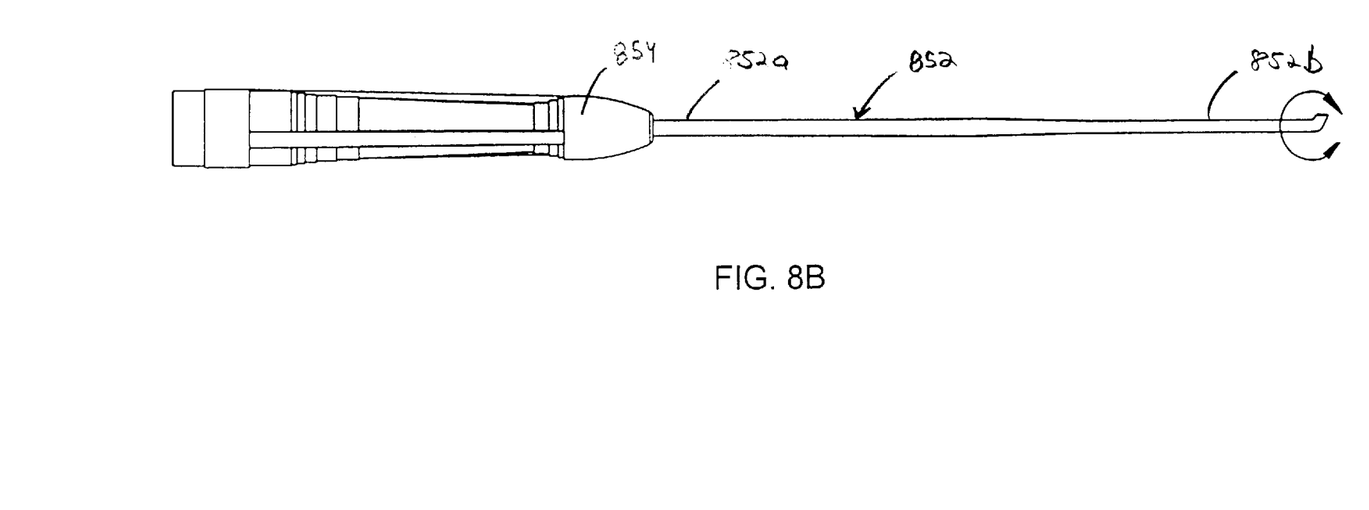
Figure 8C:
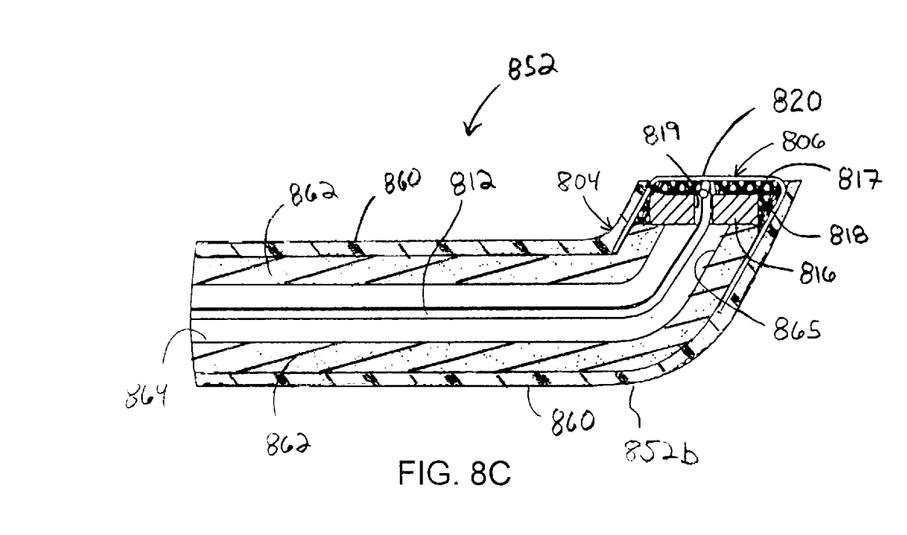

In another embodiment shown in FIGS. 8A–8C, probe 852 includes a modified distal end but is otherwise similar to the off-axis electrode embodiments shown in FIGS. 4A–E and 5A–B. Probe 852 has a proximal end 852a attached to a handle 854 and a distal end 852b having an arcuate extension 804 which terminates and forms an off-axis electrode surface 820. Handle 854 includes a suitable electrical connector for connection to a radio frequency or RF power supply. Probe 852 includes a hollow elongate probe member 862 which is made from a conductive material. An insulating material or shell 860 is provided around elongate probe member 862 in the manner described and discussed above. Radio frequency power is selectively supplied to the flat electrode surface 820 via elongate probe member 862 when the radio frequency power source is operably connected to handle 854.

An inner surface of elongate probe member 862 forms a cavity or lumen 864 which extends from the proximal end 852a to the distal end 852b of probe 852 and forms an opening 865 as shown in FIG. 8C. Although the illustrated embodiment includes an annular cavity terminating in an annular opening, one should appreciate that the cavity and opening may have other cross-sectional shapes, for example, elliptical, triangular, square, or any other polygonal shape. Alternatively, one should appreciate that the probe may instead be solid in cross-section.

A conductive extremity 806 is provided at the distal end of probe 852 and at least partially covers annular opening 865 to define the flat electrode surface 820. Conductive extremity 806 includes a perforated plate or washer 816 and a thin walled cap 817, each made from any suitable conductive material. Washer 816 is affixed to the distal extremity of arcuate extension 804 with a suitable adhesive such as epoxy 818, which is preferably conductive. One should appreciate that other suitable materials and/or means may be used to affix washer 116 and cap 117 to the distal end of probe 852. Washer 816 substantially encloses or covers annular opening 865 of arcuate extension 804 and is preferably provided with a small central aperture 819. A thermal couple 812 extends through probe lumen 864 and aperture 819 and terminates adjacent an inner surface of cap 817. Thermal couple 812 provides temperature feedback to the radio frequency power source.

Flat electrode surface 820 of the embodiment shown in FIGS. 8A–C is off-axis in a similar manner as described above in that the longitudinal axis of probe 852 is not normal to flat electrode surface 820. Instead and as shown in FIGS. 8B and 8C, a normal axis extending from flat electrode surface 820 is substantially orthogonal to the longitudinal axis of the probe 852.

Advantageously, probe 852 includes a reinforced construction which is particularly suited for the significant temperatures obtained during an electrosurgical procedure. The reinforced configuration of plate 816 and cap 817 of probe 852 minimizes any tendency of flat electrode surface 820 from popping or blowing off of the distal extremity 852b of probe 852.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A surgical instrument, comprising:
   a handle;
   an elongated probe connected to the handle and having a terminus distal to the handle;
   at least one electrode including an electrode surface positioned on the terminus so that a line from a geometric center of the electrode surface and substantially perpendicular to the electrode surface intersects at an angle a longitudinal axis formed by the elongated probe; and
   a conductor for attaching the at least one electrode to the handle,
   the elongated probe further comprising an elongated probe member having proximal and distal extremities, the handle connected to the proximal extremity, and the at least one electrode carried by the distal extremity, the probe member including a shaft having proximal and distal ends and a distal opening, the at least one electrode including a flat perforated plate and a cap, the perforated plate being fixed to the distal end of the shaft and partially covering the distal opening, the cap enclosing the perforated plate and a portion of the distal end of the shaft,
   wherein the plate is affixed to the distal end by epoxy,
   the surgical instrument further comprising a thermal couple extending through the shaft and the perforated plate, the thermal couple including a terminus located adjacent the cap.

2. The instrument of claim 1 wherein the terminus of the thermal couple is embedded in the epoxy between the perforated plate and the cap.

3. The instrument of claim 1 wherein:
   the plate includes a face and a side wall, and
   the cap encloses the plate by extending over a portion of the face and along a portion of the side wall.

4. A surgical apparatus comprising:
   a handle including a distal portion;
   an elongated probe coupled to the distal portion of the handle and including a distal portion;
   a conductive plate including a face and a side wall, the conductive plate coupled to the distal portion of the elongated probe; and
   a conductive cap electrically coupled to the plate and enclosing the plate by extending over a portion of the face and along a portion of the side wall, the cap forming an electrode surface and configured to deliver energy to tissue.

5. The apparatus of claim 4 wherein the cap encloses at least part of the distal portion of the elongated probe.

6. The apparatus of claim 5 wherein:
   the elongated probe defines a lumen and the distal portion of the elongated probe defines an opening in communication with the lumen, and
   the plate covers at least part of the opening.

7. The apparatus of claim 4 wherein:
   the elongated probe defines a lumen and the distal portion of the elongated probe defines an opening in communication with the lumen, and
   the plate covers at least part of the opening.

8. The apparatus of claim 4 wherein the plate is perforated.

9. The apparatus of claim 8 wherein the plate comprises a washer.

10. The apparatus of claim 4 wherein the plate is flat.

11. The apparatus of claim 4 wherein the cap is flat.

12. The apparatus of claim 4 further comprising epoxy to couple, at least partially, the plate to the elongated probe, and the cap to the plate.

13. The apparatus of claim 12 wherein the epoxy is conductive.

14. The apparatus of claim 4 further comprising a thermal couple coupled to the cap.

15. The apparatus of claim 4 wherein the elongated probe defines a longitudinal axis that is not normal to the electrode surface.

* * * * *

UNITED STATES PATENT AND TRADEMARK OFFICE
CERTIFICATE OF CORRECTION

PATENT NO. : 6,645,203 B2
DATED : November 11, 2003
INVENTOR(S) : Hugh R. Sharkey, Gary S. Fanton, J. Remberto Carranza and Douglas M. Lorang It is certified that error appears in the above-identified patent and that said Letters Patent is hereby corrected as shown below:

Title page,
Item [56], References Cited, U.S. PATENT DOCUMENTS, "300,155", replace "6/1884" with -- 6/1894 --.
Please add:
-- 5,599,356    4/1997  Edwards et al.
5,786,705      7/1998  Baker --.

FOREIGN PATENT DOCUMENTS
0 572 131 A1:  please replace "1/1993" with -- 12/1993.
WO 85/02762:  please replace "4/1985" with -- 7/1985.
WO 93/01774:  please replace "4/1993" with -- 2/1993.
WO 95/20360:  please replace "3/1995" with -- 8/1995.

Please delete "FR 2 645 008 3/1989".
Please add:
OTHER PUBLICATIONS
-- Auhll, Richard A., "The Use of the Resectoscope in Gynecology," Biomedical Business International, October 11, 1990, pp. 91-93.

Bosacco et al., Functional Results of Percutaneous Laser Discectomy, December 1996, pp. 825-828. --

Column 4,
Line 19, replace "ca/" with -- cal/ --.
Line 20, replace "Ωm" with -- nΩm --.

Signed and Sealed this

Thirty-first Day of August, 2004

JON W. DUDAS
*Director of the United States Patent and Trademark Office*